(12) United States Patent
Terrill

(10) Patent No.: US 12,016,781 B2
(45) Date of Patent: Jun. 25, 2024

(54) HYBRID METAL-BACKED GLENOID COMPONENT

(71) Applicant: Howmedica Osteonics Corp., Mahwah, NJ (US)

(72) Inventor: Lance N. Terrill, Rochestown (IE)

(73) Assignee: Howmedica Osteonics Corp., Mahwah, NJ (US)

( * ) Notice: Subject to any disclaimer, the term of this patent is extended or adjusted under 35 U.S.C. 154(b) by 82 days.

(21) Appl. No.: 16/943,265

(22) Filed: Jul. 30, 2020

(65) Prior Publication Data

US 2021/0030553 A1 Feb. 4, 2021

Related U.S. Application Data

(60) Provisional application No. 62/881,527, filed on Aug. 1, 2019.

(51) Int. Cl.
*A61F 2/40* (2006.01)
*A61F 2/30* (2006.01)

(52) U.S. Cl.
CPC .. *A61F 2/4081* (2013.01); *A61F 2002/30324* (2013.01); *A61F 2002/30329* (2013.01); *A61F 2002/30845* (2013.01); *A61F 2002/30878* (2013.01); *A61F 2002/30881* (2013.01); *A61F 2002/30891* (2013.01)

(58) Field of Classification Search
CPC .................. A61F 2/4081; A61F 2002/4085
See application file for complete search history.

(56) References Cited

U.S. PATENT DOCUMENTS 4,261,062 A 4/1981 Amstutz et al.
5,702,447 A 12/1997 Walch et al.
(Continued)

FOREIGN PATENT DOCUMENTS

CA 2627551 A1 5/2007
EP 1509161 B1 5/2009
(Continued)

OTHER PUBLICATIONS

Extended European Search Report including Written Opinion for EP20188529.0 dated Nov. 9, 2020; 8 pages.
(Continued)

*Primary Examiner* — Megan Y Wolf
(74) *Attorney, Agent, or Firm* — Lerner David LLP

(57) ABSTRACT

In one embodiment, a glenoid implant includes a body and a flange. The body includes a bearing surface and a bone-contacting surface opposite the bearing surface. The flange extends from the bone-contacting surface of the body to a free end. The flange has an inside facing surface that faces a center of the body and an outside facing surface that faces an outer perimeter of the body. The outside facing surface is opposite the inside facing surface and each of the inside and outside facing surfaces extend from the bone-contacting surface to the free end. The outside facing surface at the bone-contacting surface of the body is 8 mm or less from the outer perimeter of the body. The outside facing surface is tapered from the bone-contacting surface toward the free end. The inside facing surface is non-parallel to the outside facing surface.

19 Claims, 5 Drawing Sheets

(56) References Cited

U.S. PATENT DOCUMENTS

| | | | |
|---|---|---|---|
| 5,800,551 | A * | 9/1998 | Williamson ....... A61B 17/1659 623/19.11 |
| 6,699,289 | B2 | 3/2004 | Iannotti et al. |
| 7,892,287 | B2 | 2/2011 | Deffenbaugh |
| 8,080,063 | B2 | 12/2011 | Ferrand et al. |
| 8,241,367 | B2 | 8/2012 | Justin et al. |
| 8,556,980 | B2 | 10/2013 | Deffenbaugh |
| 8,690,951 | B2 | 4/2014 | Baum et al. |
| 8,721,727 | B2 | 5/2014 | Ratron et al. |
| 8,876,907 | B2 | 11/2014 | Baptista et al. |
| 8,882,845 | B2 | 11/2014 | Wirth et al. |
| 9,381,085 | B2 | 7/2016 | Axelson, Jr. et al. |
| 9,474,619 | B2 | 10/2016 | Reubelt et al. |
| 9,522,067 | B2 | 12/2016 | Frankle |
| 9,713,533 | B2 | 7/2017 | Taylor et al. |
| 9,763,798 | B2 | 9/2017 | Chavarria et al. |
| 9,814,471 | B2 | 11/2017 | Goldberg et al. |
| 9,974,658 | B2 | 5/2018 | Chudik |
| 10,537,441 | B2 | 1/2020 | Axelson, Jr. et al. |
| 10,583,014 | B2 | 3/2020 | Bertagnoli et al. |
| 2005/0261775 | A1 | 11/2005 | Baum et al. |
| 2007/0016304 | A1 | 1/2007 | Chudik |
| 2007/0142917 | A1 | 6/2007 | Roche et al. |
| 2007/0219638 | A1 | 9/2007 | Jones et al. |
| 2009/0105772 | A1 * | 4/2009 | Seebeck ..................... A61F 2/38 606/329 |
| 2009/0125113 | A1 | 5/2009 | Guederian et al. |
| 2010/0161065 | A1 * | 6/2010 | Williams, Jr. ........ A61F 2/4081 623/19.11 |
| 2010/0161066 | A1 * | 6/2010 | Iannotti ................. A61F 2/4081 606/301 |
| 2010/0249938 | A1 | 9/2010 | Gunther et al. |
| 2013/0144393 | A1 | 6/2013 | Mutchler et al. |
| 2013/0150975 | A1 | 6/2013 | Iannotti et al. |
| 2014/0180425 | A1 | 6/2014 | Katrana et al. |
| 2015/0081030 | A1 | 3/2015 | Zubok et al. |
| 2015/0272741 | A1 | 10/2015 | Taylor et al. |
| 2016/0045323 | A1 * | 2/2016 | Kovacs ................. A61F 2/4081 623/19.11 |
| 2016/0270922 | A1 | 9/2016 | Pressacco et al. |
| 2017/0014238 | A1 | 1/2017 | Reubelt et al. |
| 2017/0239058 | A1 | 8/2017 | Goldberg |
| 2017/0319348 | A1 | 11/2017 | Goldberg |
| 2017/0360456 | A1 | 12/2017 | Gunther |
| 2018/0104065 | A1 | 4/2018 | Amis et al. |
| 2018/0280151 | A1 | 10/2018 | Humphrey |
| 2020/0015830 | A1 | 1/2020 | Bonin, Jr. et al. |
| 2020/0405491 | A1 * | 12/2020 | Cleveland ............. A61F 2/4081 |

FOREIGN PATENT DOCUMENTS

| | | |
|---|---|---|
| EP | 2968655 B1 | 12/2018 |
| WO | 2007051151 A2 | 5/2007 |
| WO | 2014164265 A1 | 10/2014 |

OTHER PUBLICATIONS

"Comprehensive Total Shoulder System Featuring Comprehensive Access Glenoid Instrumentation—Surgical Technique," Zimmer Biomet Brochure, Revised Nov. 2018, pp. 2-53.

"Equinoxe Strength in Numbers," Exactech Brochure, 2019, pp. 1-20 (content available Feb. 2019, per Internet Archive at web.archive.org).

Grey et al., Preliminary Results of a Novel Hybrid Cage Glenoid Compared to an Ali-Polyethylene Glenoid in Total Shoulder Arthroplasty, Bulletin of the Hospital for Joint Diseases, Dec. 2015, pp. S86-S91, vol. 73 (Suppl I).

Gulotta et al., No Differences in Early Results of a Hybrid Glenoid Compared With a Pegged Implant, Clinical Orthopaedics and Related Research, published online Sep. 2015, 7 pages.

Nelson et al., Five-year minimum clinical and radiographic outcomes of total shoulder arthroplasty using a hybrid glenoid component with a central porous titanium post, Journal of Shoulder and Elbow Surgery, Aug. 2018, pp. 1462-1467, vol. 27.

McLendon PB, Schoch BS, Sperling JW, Sánchez-Sotelo J, Schleck CD, Cofield RH. Survival of the pegged glenoid component in shoulder arthroplasty: part II; Journal of shoulder and elbow surgery; Aug. 2017; 26(8):1469-76.

Papadonikolakis A, Neradilek MB, Matsen III FA. Failure of the glenoid component in anatomic total shoulder arthroplasty: a systematic review of the English-language literature between 2006 and 2012; JBJS; Dec. 18, 2013; 95(24):2205-12.

* cited by examiner

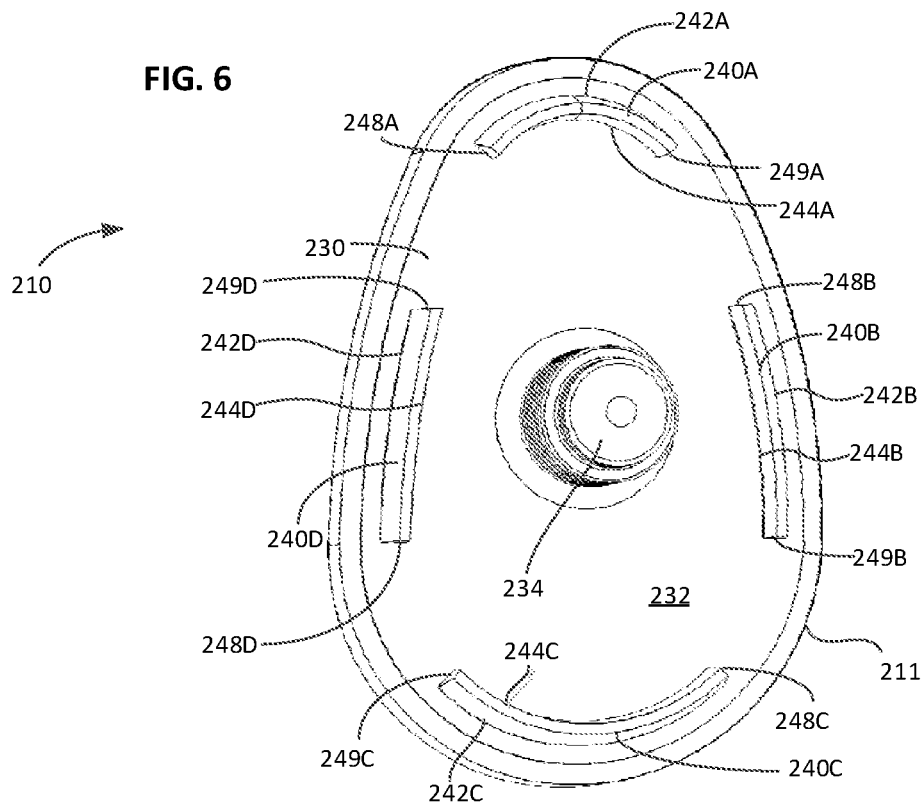
FIG. 6
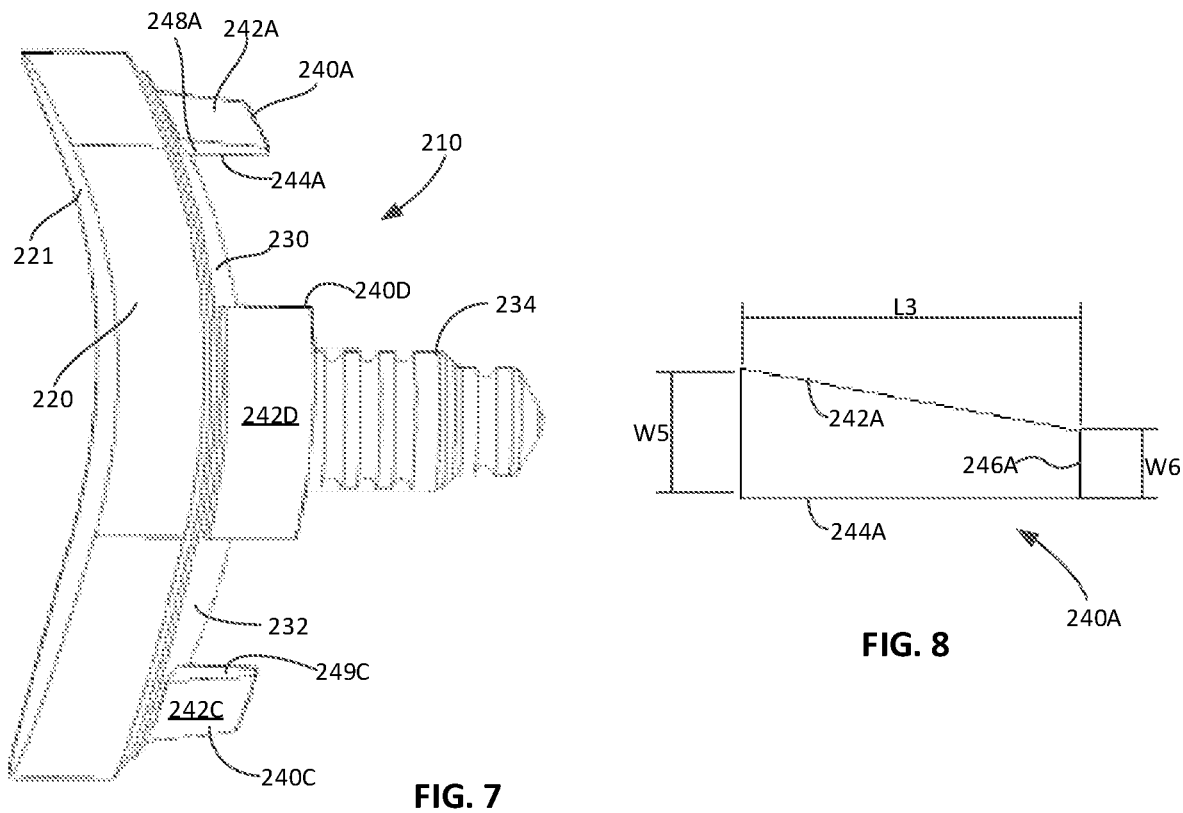
FIG. 7
FIG. 8 ental Patent Application No. 62/881,527, filed Aug. 1, 2019, the disclosure of which is hereby incorporated by reference herein in its entirety.

HYBRID METAL-BACKED GLENOID COMPONENT

CROSS REFERENCE TO RELATED APPLICATION

This application claims the benefit of the filing date of U.S. Provisional Patent Application No. 62/881,527, filed Aug. 1, 2019, the disclosure of which is hereby incorporated by reference herein in its entirety.

BACKGROUND OF THE DISCLOSURE

To improve the viability and lifespan of implants used as part of shoulder arthroplasty procedures, various designs have been developed including fully polyethylene glenoid implants and metal backed glenoid implants. However, in each of these designs, whether adapted for manual press fit into bone or for machine placement, bone cement has often been used to provide terminal securement between the implant and the bone. Over time, stress on the implant, e.g. due to the eccentric loading occurring through regular use of the shoulder, tends to weaken the cement mantle of these implants, ultimately increasing the risk of premature failure.

In some glenoid implant designs, the implant includes flanges for engagement to the bone, the flanges being located somewhat centrally at a distance from a periphery of the implant. Because the glenoid vault tends to narrow, i.e., taper, below the glenoid surface, flanges extending into the bone become closer to the cortical bone the farther the flange extends into the bone. Thus, one reason for positioning the flanges closer to the implant center is that it prevents the flanges from piercing or otherwise contacting the cortical bone of the glenoid vault when installed on the glenoid. However, glenoid implants with centrally positioned flanges as described above have led to shortened lifespans for glenoid implants. In particular, the relatively central location of the flanges in these designs has limited the load distribution through the glenoid implant and its resistance to rocking forces in the superior-inferior direction when the implant is secured in place and in use.

As the above description demonstrates, although improvements have been made in implant designs for shoulder arthroplasty, survival of glenoid implants, even with recent designs, drops considerably over time. Indeed, McLendon et al., *Survival of the pegged glenoid component in shoulder arthroplasty: part II*, 26 J. SHOULDER ELBOW SURG. 1469-1476 (2017), described the results of a study finding a clinical survival rate for glenoid implants of only 83% 10 years following original implantation.

Thus, a need exists for shoulder implants that have improved wear resistance and longevity.

BRIEF SUMMARY

In one aspect, the present disclosure relates to a glenoid implant. In one embodiment, the glenoid implant includes a body and a flange. The body includes a bearing surface and a bone-contacting surface opposite the bearing surface. The flange extends from the bone-contacting surface of the body to a free end and includes an inside facing surface that faces a center of the body and an outside facing surface that faces an outer perimeter of the body. The outside facing surface of the flange is opposite the inside facing surface, and each of the inside and outside facing surfaces extend from the bone-contacting surface to the free end. The outside facing surface at the bone-contacting surface of the body may be 8 mm or less from the outer perimeter of the body. The outside facing surface may be tapered from the bone-contacting surface toward the free end. The inside facing surface may be non-parallel to the outside facing surface.

In some examples, the inside facing surface of the flange may be substantially perpendicular to a plane extending in a superior to inferior direction of the glenoid implant. In some examples, the implant may include second, third and fourth flanges, each flange extending from a periphery of the bone-contacting surface of the body. In some examples, two of the four flanges may be respectively positioned at superior and inferior ends of the glenoid implant when implanted in the shoulder joint and the other two of the four flanges may be respectively positioned at anterior and posterior ends of the glenoid implant when implanted in the shoulder joint. In some examples, the outside facing surface of the flange at the bone-contacting surface of the body may be between 2 mm and 6 mm from the outer perimeter of the body. In some examples, the outside facing surface of the flange at the bone-contacting surface of the body may be approximately 4 mm from the outer perimeter of the body. In some examples, the outside facing surface may be planar from the bone-contacting surface to the free end. In some examples, the outside facing surface may be arcuate from the bone-contacting surface to the free end. In some examples, the outside facing surface may include two separate planar surfaces between the bone-contacting surface and the free end.

In some examples, the flange has a thickness measured from the inside facing surface to the outside facing surface, and the thickness may be within a range of 3 mm to 5 mm at the bone-contacting surface of the body and within a range of 2 mm to 4 mm at the free end of the flange. In some examples, the inside facing surface and the outside facing surface are connected by side surfaces, and a distance between the side surfaces may be within a range of 2 mm to 4 mm. In some examples, the flange has a thickness measured from the inside facing surface to the outside facing surface and the thickness may be within a range of 0.75 mm to 1.75 mm at the bone-contacting surface of the body and within a range of 0.25 mm to 1.00 mm at the free end of the flange. In some examples, the inside facing surface and the outside facing surface are connected by side surfaces, and a distance between the side surfaces may be within a range of 5 mm to 15 mm. In some examples, the free end of the flange may be pointed. In some examples, the flange has a length extending from the bone-contacting surface to the free end and the length may be within a range of 4 mm to 10 mm.

In one embodiment, a glenoid implant includes an outer layer, an inner layer and a flange. The outer layer has a first material property and is configured to articulate with a first native or prosthetic bone of the shoulder joint. The inner layer is fixed to the outer layer and is adapted for engagement with a bearing surface of a second bone of the shoulder joint. The inner layer has a second material property different from the first material property. The flange extends from an inner surface of the inner layer and has an outside facing surface that faces an outer perimeter of the inner layer and an inside facing surface that faces a center of the inner layer. The outside facing surface is generally coincident with a first plane and the inside facing surface is generally coincident with a second plane. The first plane and the second plane are non-parallel.

In some examples, the implant may include second, third and fourth flanges, where each flange extends from the inner surface of the inner layer. In some examples, the inside facing surfaces of two of the first, second, third and fourth flanges may be parallel to one another. In some examples, the outside facing surfaces of each of the first, second, third and fourth flanges may be tapered toward respective free ends of the flanges relative to the inside facing surfaces of the flanges. In some examples, the outside facing surface of the flange at the inner surface of the inner layer may be 6 mm or less from an outer edge of the outer layer. In some examples, the outer layer may be a polymer and the inner layer may be a metal. In some examples, the inner layer may include a sublayer with a lower modulus of elasticity than a remainder of the inner layer. In some examples, the inner layer may include a central opening therethrough such that a central post of the outer layer passes through the central opening. The central post may be configured to be inserted into the second bone of the shoulder joint. In some examples, the central opening may have a perimeter with a clover shape.

In another aspect, the present disclosure relates to an implant for use in a mammalian joint. In one embodiment, the implant includes an outer layer, an inner layer and a flange. Both the outer layer and the inner layer have a joint facing surface and a bone facing surface. The joint facing surface of the inner layer is fixed to the bone facing surface of the outer layer. The flange has a length that extends from the bone facing surface of the inner layer to a free end. Additionally, the flange includes an outside surface that faces an outer perimeter of the inner layer and an inside surface that faces a center of the inner layer. The inside surface is opposite the outside surface, and both the inside surface and the outside surface extend along the length of the flange. The outside surface of the flange at the bone facing surface may be 8 mm or less from an outer perimeter of the outer layer. The outside surface and the inside surface may be asymmetric about a central longitudinal axis of the flange.

In some examples, the flange may have a decreasing sectional dimension from the bone facing surface of the inner layer to the free end. In some examples, the outside surface of the flange at the bone facing surface may be 2 mm to 6 mm from the outer perimeter of the outer layer. In some examples, the outside surface of the flange at the bone facing surface is a first distance from both the outer perimeter of the inner layer and the outer perimeter of the outer layer.

In yet another aspect, the present disclosure relates to a method of fixing a glenoid implant onto a glenoid bone. In one embodiment, the method includes: advancing the glenoid implant onto a bone surface of the glenoid bone, a plurality of flanges of the glenoid implant advancing through the bone surface, each of the plurality of flanges having a tapered shape such that a displacement of bone material increases as each flange advances. During advancement of the glenoid implant, an outside surface of each of the plurality of flanges, the outside surface defining the tapered shape, becomes closer to an inner cortical bone surface of the glenoid bone.

In some examples, advancing the glenoid implant may involve directing each of the plurality of flanges closer to a tangent position relative to the inner cortical bone surface. In some examples, the method may include preparing at least one pilot hole for each of the plurality of flanges. In some examples, advancing the plurality of flanges through the bone surface may involve piercing the bone surface with a pointed tip of each of the flanges.

In yet another aspect, the present disclosure relates to a method of preparing a glenoid bone for implant placement. In one embodiment, the method includes: identifying a location on a glenoid bone surface for insertion of a flange of a glenoid implant; and creating holes in the glenoid bone to aid in the insertion of the flange by: drilling a first pilot hole on a first trajectory relative to a glenoid surface; and drilling a second pilot hole adjacent to the first pilot hole, the second pilot hole having a second trajectory angled relative to the first trajectory.

In some examples, drilling of the first pilot hole and the second pilot hole does not create an overlap between the respective pilot holes within the bone. In some examples, drilling the second pilot hole may involve aligning a drill so that the second trajectory is offset from an inner cortical bone surface of a cortical bone defining a glenoid vault at least to a depth of 10 mm below a surface of the glenoid bone. In some examples, advancing the flange into the glenoid bone may proceed such that a tapered surface of the flange is parallel with the second pilot hole.

BRIEF DESCRIPTION OF THE DRAWINGS

The present disclosure will be better understood on reading the following detailed description of non-limiting embodiments thereof, and on examining the accompanying drawings, in which:

FIGS. 6 and 7 are rear and side views, respectively, of a glenoid implant according to one embodiment of the disclosure;

FIG. 8 is a side view of a flange of the glenoid implant of FIG. 6;

DETAILED DESCRIPTION

In one aspect, the present disclosure relates to a joint replacement implant. Although described throughout the disclosure with specific application to the glenoid, it should be appreciated that the implants, kits and methods described herein may be employed in other joints of the body, such as the hip. Additionally, it should also be appreciated that in some embodiments of the present disclosure, patient-specific glenoid implant shapes may be derived from a proprietary population-based orthopedic design and development system by Stryker®: Stryker Orthopaedic Modeling and Analytics (SOMA). As used herein in reference to a glenoid implant, the term "superior" refers to a portion of the implant nearer the patient's head, while the term "inferior" refers to a portion of the implant nearer the user's feet, when the implant is implanted in an intended position and orientation. As with the terms "superior" and "inferior," the term "anterior" refers to a portion of the implant nearer the front of the patient, the term "posterior" refers to a portion of the implant nearer the rear of the patient, the term "medial" refers to a portion of the implant nearer the mid-line of the patient, and the term "lateral" refers to a portion of the implant farther away from the mid-line of the patient.

Figure 1:
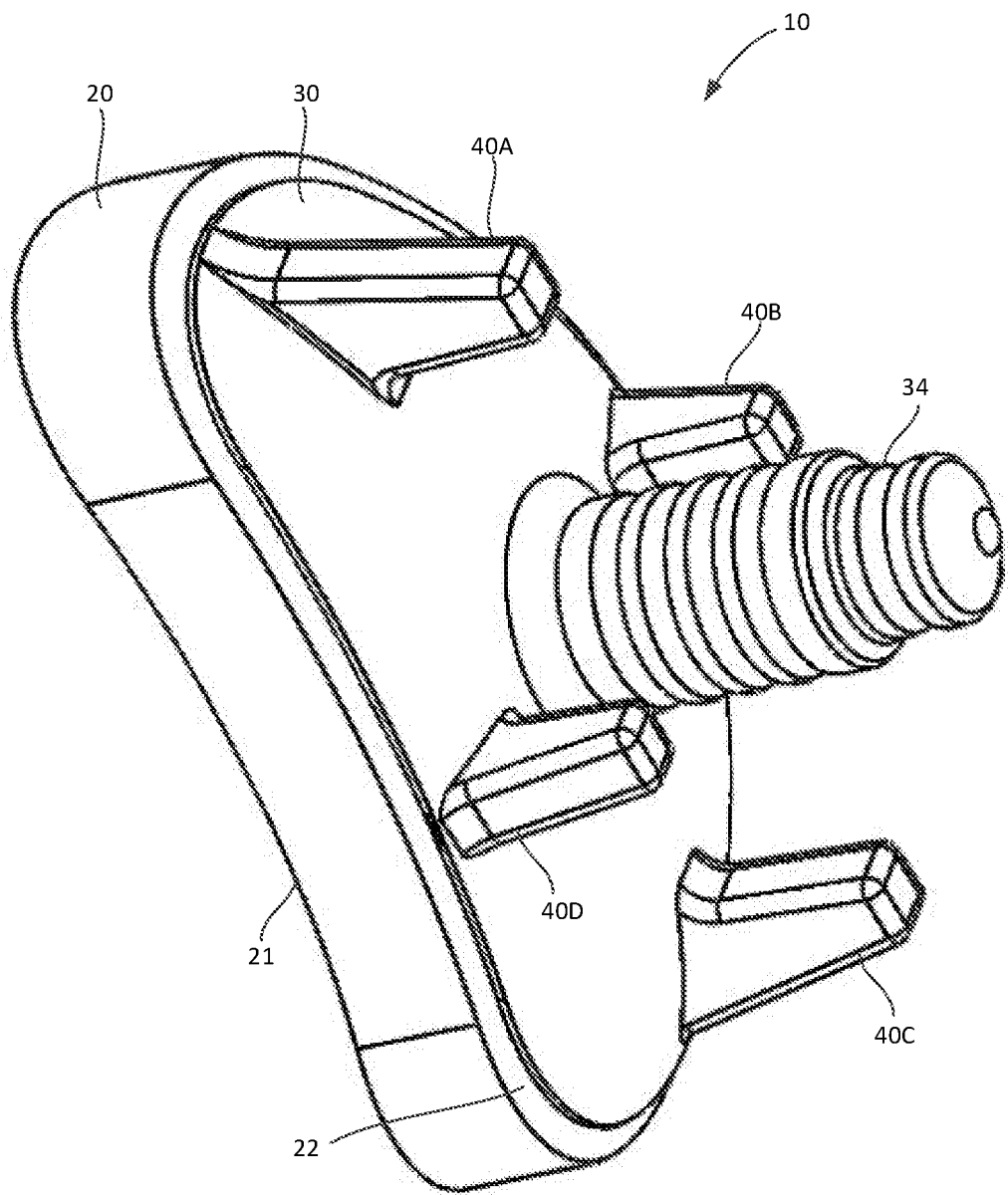
FIG. 1 is a perspective view of a glenoid implant according to one embodiment of the disclosure.
Figure 3:
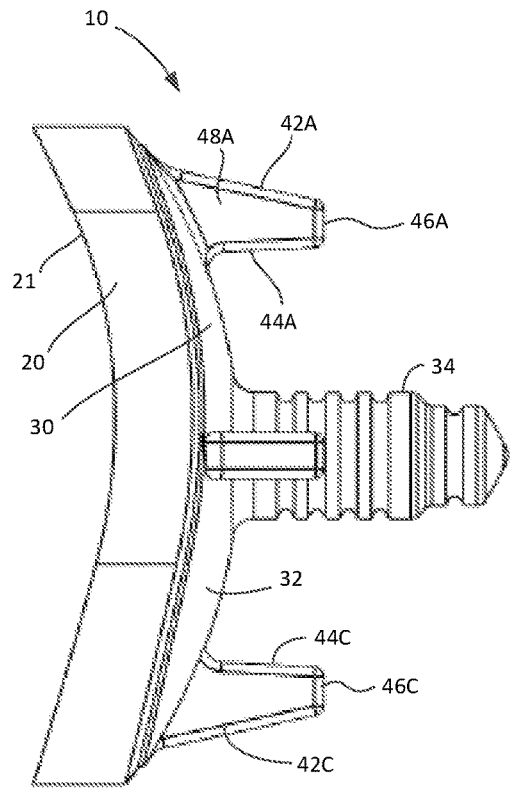

One embodiment of a glenoid implant 10 is shown in FIG. 1. Implant 10 includes two layers, an outer polymer layer 20 and an inner metal layer 30. In some examples, polymer layer 20 is molded onto metal layer 30. When positioned in a shoulder joint, polymer layer 20 is positioned laterally while metal layer 30 is positioned medially. The outer polymer layer 20 includes an outer surface 21 with contours that correspond to a natural articulating surface of a glenoid. Outer surface 21 is intended to articulate with respect to a native or prosthetic humeral head of the shoulder joint. An inner surface 22 of polymer layer 20 abuts and interfaces with metal layer 30. The polymer of the polymer layer 20 may be an ultra-high-molecular-weight polyethylene (UHMWPE), although other biocompatible polymers may be suitable for polymer layer 20. Metal layer 30 includes an outward facing surface that abuts and interfaces with polymer layer 20. An inner surface 32 of metal layer 30 has a generally convex surface, as shown in FIG. 3, although in variants, the contours of the inner surface may vary. Inner surface 32 is intended to contact the surface of a native or prepared glenoid, and thus may also be referred to as a bone-contacting surface. A surface area of inner surface 32 may be slightly less than a surface area of inner surface 22 of polymer layer 20, defining a lip. In variations, the lip may be greater or lesser than the amount shown in the depicted embodiment. Extending in an inward, i.e., medial direction from inner surface 32 are post 34 at a center of the inner surface and four flanges 40A-D positioned at spaced apart peripheral locations of the metal layer and substantially parallel to a central axis through post 34. The inclusion of four flanges may be advantageous in that such quantity is sufficient to produce a stable fixation between the implant and the bone while also being small enough in number so as not to overly complicate the shoulder arthroplasty procedure.

Post 34 includes a plurality of annular ridges and troughs and has a tapered tip, as shown in FIG. 3. The grooves in post 34 are sized and spaced to optimize the functionality of the post as a securement mechanism when cement is deposited around the surface of the post. Post 34 extends from inner surface 32 of metal layer 30 to a free end and may be made of the same material as the metal layer.

Figure 2:
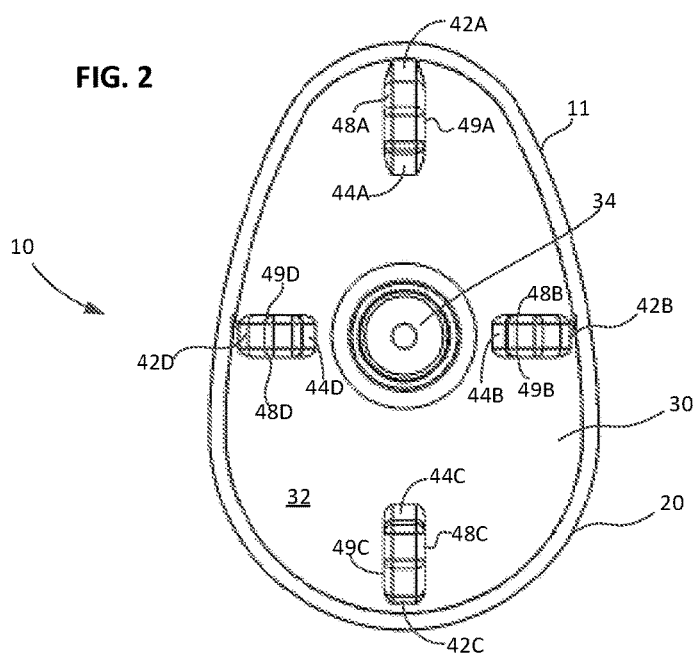
FIGS. 2 and 3 are rear and side views, respectively, of the glenoid implant of FIG. 1.
Figure 14:
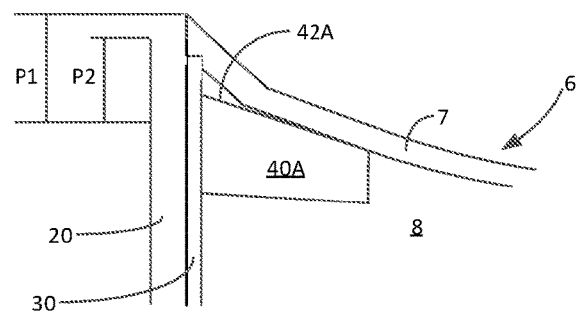

As best shown in FIGS. 1-3, implant 10 includes four flanges 40A-D extending from inner surface 32 of metal layer 30. Each flange may be an extension of metal layer 30 and may be made of the same material. Flange 40A will now be described. It should be appreciated that flange 40A is representative of all of the flanges in this embodiment and accordingly flanges 40B-40D may have substantially the same features. Additionally, it should be understood that when implant 10 is implanted in a shoulder, flange 40A is a superior flange, while flange 40C is an inferior flange, and flanges 40B and 40D may be anterior or posterior flanges depending on which side of the patient the implant is implanted. Thus, although the features described with respect to flange 40A may be substantially the same as flanges 40B-D, it should be understood that the orientation of those features may be different for the differently positioned flanges 40B-D. Flange 40A is located immediately adjacent to a periphery, i.e. perimeter of implant 10. In some examples, an outside (or superior) surface 42A of the flange at the inner (or medial) surface 32 is anywhere from 0 mm to 8 mm from outer edge 11 of implant 10. In some examples, outside surface 42A is in a range from 3 mm to 4 mm from outer edge 11. In some examples, outside surface 42A is no more than 2 mm from outer edge 11. In still further examples, outside surface 42A is no more than 1.5 mm from outer edge 11. In other examples, the SOMA system may provide guidance regarding an appropriate distance between the flange and the outer edge. The aforementioned distance, or dimension, is also shown in FIG. 14 and described elsewhere in the present disclosure as P2.

Figure 4:
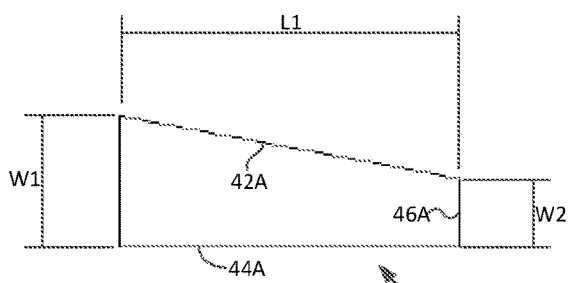
FIG. 4 is a side view of a flange of the glenoid implant of FIG. 1.

Flange 40A includes inside (or inferior) surface 44A facing a center of the implant, outside (or superior) surface 42A opposite the inside surface and facing a perimeter of the implant, side (or anterior/posterior) surfaces 48A, 49A separating the inside and outside surfaces, and a free end (or medial) surface 46A remote from the inner surface 32 of metal layer 30. A detail of flange 40A is shown in FIG. 4. Flange 40A tapers from a base at inner surface 32, where a width, also referred to herein as a thickness, of flange 40A is W1, to free end 46A, where a width of flange 40A is W2. In particular, outside surface 42A is tapered. In this manner, outside surface 42A and inside surface 44A are non-parallel with respect to one another. Additionally, and as shown in FIGS. 3 and 4, outside surface 42A is substantially planar. In some examples, outside surface 42A is at an angle in a range from about 5° to about 25° relative to inside surface 44A. In some examples, inside surface 44A is substantially perpendicular to a plane extending in a superior to inferior direction of the implant. In some examples, inside surface 44A is substantially planar. In some examples, the inside surface of each flange is parallel with respect to one or more of the other flanges and/or at right angles with respect to one or more of the other flanges. In some examples, W1 is within a range from about 3 mm to about 5 mm. In some examples, W2 is within a range from about 2 mm to about 4 mm. In one specific example, W1 is about 3 mm and W2 is about 2 mm. It is envisioned that various combinations of W1 and W2 are possible provided that such dimensions produce a tapered outside surface 42A. A dimension between side surfaces 48A, 49A may be within a range from about 2 mm to about 4 mm. A length of flange 40A is represented by L1. In some examples, L1 is within a range from about 2 mm to about 10 mm. This range may be advantageous in that it may provide for blood vessel penetration within the bone on the inside of the implant. In further examples, L1 is within a range from about 4 mm to about 6 mm. An optimal value for L1 may be longer if resistance to bending moment is a concern upon loading of the implant while, conversely, an optimal value may be shorter in circumstances where revision surgery is considered as likely in the future. Advantages of implant 10 when used in the shoulder are more pronounced when flanges have an L1 of at least about 4 mm. It should be appreciated that although outside surface 42A of flange 40A is planar, the outside surface may also be defined by other surfaces, such as an arcuate, i.e., concave or convex surface, a series of stepped surfaces, or two or more planar surfaces bridging a distance along the length of the flange from the base to the free end. In many examples, the outside surface of the flange is non-parallel to the inside surface. In the aforementioned examples, including examples where outside surface of the flange is planar, the outside surface and the inside surface are asymmetric about a central longitudinal axis of the flange. Additionally, the tapered geometry of the flanges has a cross-sectional dimension that decreases from the bone facing surface of the inner layer to the free end.

The positioning of the flanges on implant 10 may be advantageous because it may allow for bone ingrowth around the periphery of the glenoid vault via the flanges when the implant is in position fixed to the glenoid. This provides greater load distribution over the surface area of the implant. Additionally, the location of the flanges along the perimeter of the implant provides increased contact area along the perimeter, thereby providing better peripheral stress transfer. Where the implant has flanges that secure at superior and inferior ends of the glenoid, as with implant 10, described in greater detail in the description accompanying FIGS. 11-14, there is increased contact area at the superior and inferior ends, thereby mitigating superior-to-inferior rocking of the implant while it is fixed to the bone. Yet another advantage is derived from the symmetry of implant 10 in the superior-to-inferior axis. Due to this symmetry, the implant may be used in either the right or left shoulder of a patient. It should be appreciated, however, that in some examples, it may be desirable to use an implant designed with flanges positioned in a manner that favors placement of the implant specifically in the right or left shoulder. For instance, in a surgery planned with use of the SOMA system, SOMA may determine, based on its anatomical database and the surgery at issue, that an optimal implant may have geometry tailored for the shoulder being operated upon (i.e., right or left).

Figure 5:
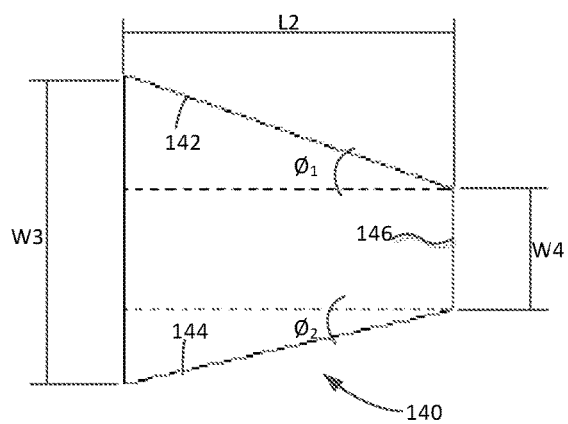
FIG. 5 is a side view of a flange of a glenoid implant according to one embodiment of the disclosure.

In a variation of implant 10, one or more of the flanges include an inward taper such that the inside surface of the flange is tapered. One example of this is shown in FIG. 5 for flange 140. Unless otherwise stated, like reference numerals refer to like elements in implant 10, but within the 100 series of numerals. Width and length possibilities for flange 140 may be any of those contemplated for flanges 40A-D. Thus, for example, W3 may be in a range from about 3 mm to about 5 mm and W4 may be in a range from about 2 mm to about 4 mm. Further, in other examples, W3 and W4 may have dimensions larger than the values within these ranges in view of the dual taper structure. In flange 140, both inside 144 and outside 142 surfaces are tapered toward free end 146. The taper of outside surface 142, having an angle $\theta_1$, is steeper than the taper of inside surface 144, having an angle $\theta_2$. In some examples, $\theta_1$ is in a range from about 5° to about 25°. In some examples, $\theta_1$ is in a range from about 10° to about 15°. In some examples, $\theta_1$ is in a range from about 12° to about 13°. In some examples, $\theta_2$ is in a range from about 1° to about 5°. In some examples, $\theta_2$ is in a range from about 2° to about 4°. The inclusion of the taper on inside surface 144 is advantageous in that it may render insertion of the implant into bone easier than it would be otherwise with flanges absent such additional taper.

In the embodiments shown in FIGS. 1-5, the metal layer 30 may be a metal characterized as having three sublayers: outer and inner sublayers and a central layer between the outer and inner sublayers. The outer and inner sublayers are foam-like and have higher porosity than the central layer. In one example, the metal may be a porous titanium. In some examples, a depth, i.e., thickness, of each of the inner and outer sublayers may be at least 0.5 mm. Consistent with the above described properties, the outer and inner sublayers also have a lower modulus of elasticity than the central sublayer. The properties of the metal layer render the combination of the metal and polymer layers conducive to molding, as well as enhancing bone ingrowth into the metal layer after implantation. In some examples, the metal layer and the polymer layer are molded together via injection molding. For example, the metal layer 30 may be formed first, and may be inserted into a mold having the desired shape for the polymer layer 20. The mold may include a liquid polymer, and the liquid polymer may solidify into the desired shape onto the metal layer 30. In other examples, the metal layer and/or the polymer layer may have properties that allow for other securement modalities. Such alternative modalities may include press-fit between the polymer layer and the metal layer. For instance, the implant components may include positive locking features so that the implant may be assembled via a machine press-fit. In some examples, additive manufacturing may be used to produce one or more of the metal layer and the polymer layer.

In some embodiments, the metal layer of the implant is a solid metal, e.g., a metal with less porosity (i.e., greater density) than the metal layer of implant 10. A solid metal may be, for instance, a titanium or a titanium alloy with a density of 99% or more. Here, the percentage density is indicative of the lack of porosity in the solid metal. One example of such an embodiment is shown in FIGS. 6-8. Unless otherwise noted, like reference numerals refer to like elements of implant 10, but within the 200 series of numerals. Implant 210 includes polymer layer 220 and metal layer 230. Extending from inner surface 232 of metal layer 230 are central post 234 and four flanges 240A-D. Flange 240A will now be described, and it should be appreciated that in the depicted embodiment, flange 240A is representative of flanges 240A-D, with the exception of the different orientations of the flanges. Relative to flange 40A, flange 240A is narrower in width, i.e., thickness, measured from the inner surface 244A to the outer surface 242A, and has a peripheral dimension longer than that of flange 40A, measured from one side surface to the other, 248A to 249A. As shown in FIG. 6, the peripheral dimension is curved for flange 240A. This curve is shaped to be in parallel with a perimeter of the implant itself, such as a perimeter of inner layer 230. In this manner, a radius of curvature for the peripheral dimension of flange 240A (and 240C) is smaller than a radius of curvature for either of flanges 240B, 240D. In an alternative configuration, the curvature of the peripheral dimension of one or more flanges may generally correspond to the outer perimeter of the implant without being exactly parallel. A width of flange 240A is W5 at inner surface 232 and W6 at free end 246A. In some examples, W5 is within a range from about 0.75 mm to about 1.75 mm. In some examples, W6 is within a range from about 0.25 mm to about 1.00 mm. In one specific example, W5 is about 0.75 mm and W6 is about 0.25 mm. It is envisioned that various combinations of W5 and W6 are possible provided that such dimensions produce a tapered outside surface 242A. Turning to the peripheral dimension, in some examples, the peripheral dimension between side surfaces 248A, 249A is within a range from about 5 mm to about 15 mm. In some examples, L3, a length of flange 240A, is within a range from about 2 mm to about 10 mm.

Flanges 240A-D are shaped, as shown in FIG. 7, to have sharp pointed tips at their respective free ends, thereby functioning as blades to provide an improved ability to penetrate bone. In this manner, implant 210 is advantageous in that it may be press fit into a glenoid bone via penetration of flanges 240A-D into the bone without the need for initially drilling pilot holes into the bone for receipt of the flanges. Another advantage of using implant 210 is that bone ingrowth into flanges 240A-D is less than with implant 10 due to the reduced porosity in the metal layer, thereby rendering it easier to remove implant 210 if revision or replacement is necessary at a later date. In variations of implant 210, any number of flanges may be included. The unique geometry of flanges 240A-D renders the inclusion of a larger number of flanges practical for at least the reason that drilling of pilot holes is not required to prepare the glenoid vault for receipt of the implant. In this manner, implant 210 may have one, two, three, six, eight or more flanges, for example. In one specific variation where the implant includes a single flange, such flange may be a continuous structure parallel to and offset from a perimeter of the implant. In some embodiments, an implant that includes a solid metal layer may have flanges shaped and positioned as described for the implant shown in FIG. 1. Similarly, in some alternative arrangements, any implant described herein may include a metal layer, i.e., the metal component of the implant, that is either solid or porous.

Figure 9:
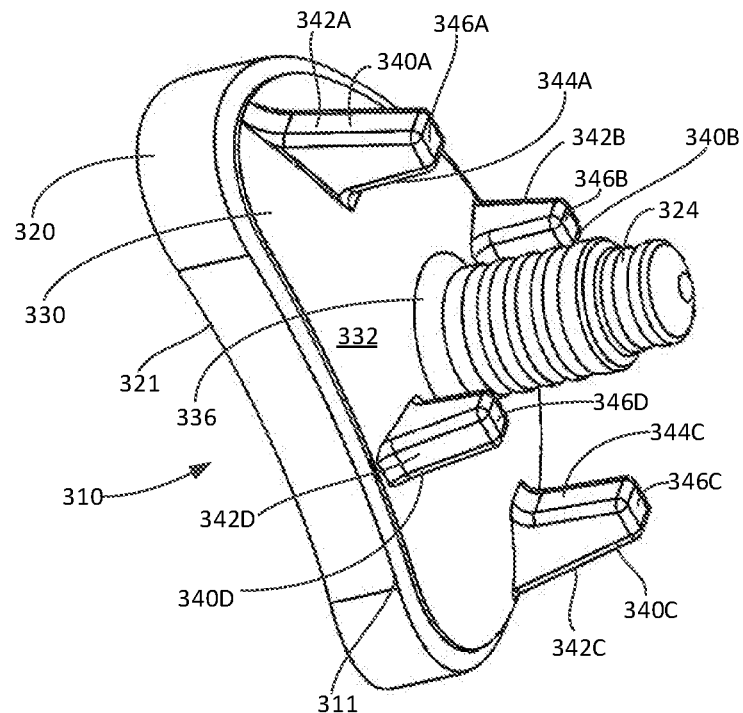
FIG. 9 is a perspective view of a glenoid implant according to one embodiment of the disclosure.
Figure 10:
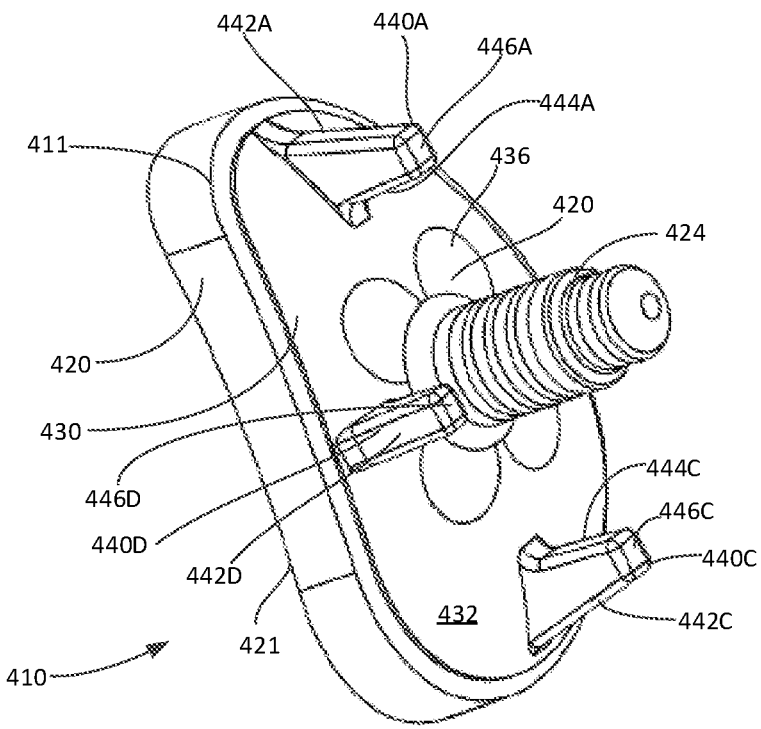
FIG. 10 is a perspective view of a glenoid implant according to one embodiment of the disclosure.

In some embodiments, a central post of the implant is part of the polymer layer 320, as shown in FIG. 9. Unless otherwise noted, like reference numerals refer to like elements of implant 10, but within the 300 series of numerals. Polymer layer 320 of implant 310 includes central post 324. To position metal layer 330 onto polymer layer 320, metal layer 330 includes an opening 336 therethrough. In other embodiments, the central post may be part of the polymer layer, but distinguishable from implant 310, such as is shown in FIG. 10. Again, unless otherwise noted, like reference numerals refer to like elements of implant 10, but within the 400 series of numerals. Metal layer 430 includes opening 436 with a size sufficient for central post 424 to be disposed therethrough. In this arrangement, opening 436 is clover-shaped, with a series of part-circular shapes that define a perimeter of opening 436. In variations of implants 310, 410, the central opening through the metal layer of the implant may be a different size than shown in the depicted embodiments and may have a perimeter with a different pattern. For example, a perimeter of a metal layer central opening may be star shaped, diamond shaped or square shaped. Designs with a central post forming part of the polymer layer are advantageous in that the polymer post of such implants may be cut or drilled out with relative ease compared to a metal post in order to perform a revision surgery, for example. Additionally, such an arrangement is also advantageous in that the overall construct has less stiffness when the central post is a polymer instead of a metal. Nonetheless, there is still significant surface area contact between the metal layer and the bone in these arrangements, and because of the greater surface area contact between the metal and bone, there is improved the fixation between the two.

The glenoid implant may be varied in many ways. With regard to the flanges in particular, the implant may include three flanges or five or more flanges. One or more of the total number of flanges may be placed adjacent to the periphery, i.e., perimeter of the implant. In some examples, the flanges of the implant may be arranged in specific patterns. For example, an implant that includes six flanges may have three equidistant flanges at a superior end of the implant and three equidistant flanges at an inferior end of the implant. Turning to the geometry of the flanges themselves, it should be appreciated that a single implant may include two or more unique flange types, e.g., shapes, lengths, etc. A particular flange may have an outside surface with a taper in the form of an arc. The arc may be concave or convex in a direction of a length of the flange. In some examples, the taper may include a series of flat steps toward the free end of the taper. In some examples, the taper may include one or more tapered segments in combination with non-tapered segments. In some examples, up to four sides of the flange, each side extending between the base of the flange and its free end, may be tapered. In this manner, a flange may be tapered on all of its sides.

In another aspect, the present disclosure relates to a method of positioning and fixing an implant onto a prepared glenoid surface. One embodiment of the method is shown in FIGS. 11-14 and involves fixation of implant 10 to the glenoid.

The method begins with a glenoid surface prepared for implant placement. To prepare the glenoid surface for the geometry of the implant, a central pilot hole (not shown) is drilled at a central location on the glenoid. Drilling may be directly into bone or via insertion of an initial pilot wire followed by reaming. Preparation of the glenoid surface may involve reaming of the glenoid surface or other actions so that the surface is ready for implant placement. Thus, for example, if it is necessary to form grooves in the glenoid surface, then such grooves may be machined out by a guide and drill combination or with a bur. The exact details of the surface preparation steps may vary and precede the steps pertinent to the described method of the present disclosure. When the glenoid surface is ready, the placement location of implant 10 on glenoid 4 is verified so that pilot holes for the flanges may be drilled. The location for the pilot holes may be identified through marking on the glenoid surface or other known techniques.

Figure 11:
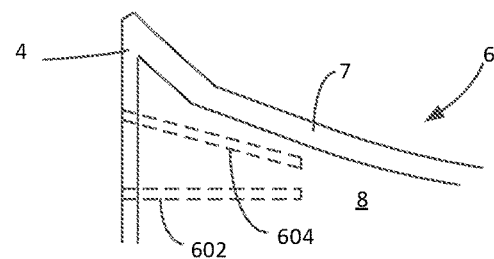
FIGS. 11-14 show steps in a method of placing and securing a glenoid implant into a glenoid bone according to one embodiment of the disclosure.

Prior to placement of implant 10, pilot holes are drilled at locations on the glenoid that will receive one of the flanges 40A-D. These pilot holes are created in cancellous bone 8 in a glenoid vault 6 of the patient's shoulder. For each flange, two pilot holes are drilled. One example of this is shown in FIG. 11, where reference numerals 602 and 604 indicate pilot holes prepared for receipt of flange 40A. Due to the tapered shape of each of flanges 40A-D, pilot hole 602 is roughly orthogonal to a surface of glenoid 4, while pilot hole 604 is angled to approximate the taper of the flange. In this manner, each pilot hole is created by positioning a drilling tool along a unique trajectory. It should be appreciated that the exact alignment of each pilot hole may vary to complement the specific geometry of the flanges on the implant. In some examples, such as with holes 602, 604, the first pilot hole does not overlap with the second pilot hole adjacent to the first pilot hole. For implant 10 with four flanges 40A-D, four pairs of pilot holes in total are created in the above manner, two for receipt of each flange. In some alternative approaches, a single pilot hole is drilled for each flange. In some alternative approaches, drilling may involve insertion of a pilot wire and then reaming over the pilot wire to create pilot holes. In other alternative approaches, a broach technique may be used in place of drilling for one or more of the pilot holes and the central pilot hole. The accuracy of each pilot hole may be verified at this time at the discretion of the surgeon.

Figure 12:
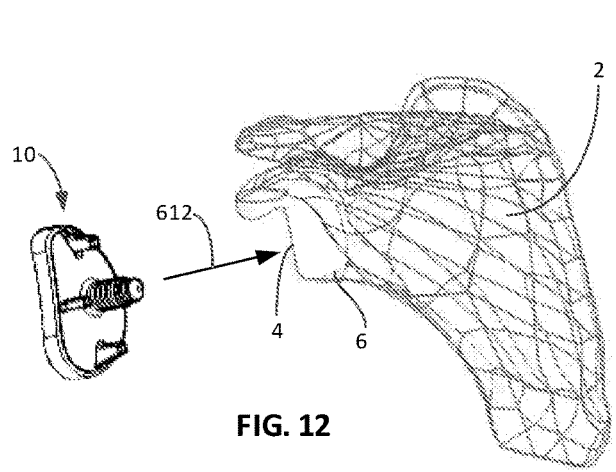

Next, implant 10 is ready for advancement, positioning, and fixation to glenoid 4. In this step, the implant is advanced into position on the glenoid manually by hand. Alternatively, insertion instruments and other aids may also be employed at the discretion of the surgeon. In FIG. 12, reference numeral 612 indicates the advancement of implant 10 onto glenoid surface 4, with scapula 2 of the patient shown for greater context. Upon contact with the bone surface of glenoid vault 6, each flange 40A-D advances into vault 6 aided by the pilot holes corresponding to each flange. And, similarly, central post 34 advances into central pilot hole in glenoid vault 6. In some examples, bone cement is first prepared and placed in the central pilot hole prior to advancement of the implant into glenoid vault 6. In other examples, cement is placed around post 34 prior to advancement of the implant into glenoid vault 6. In some examples, the outside facing surfaces of the flanges facing a perimeter of the implant become closer to an inner cortical bone surface of the glenoid vault as the flanges are advanced into the bone. In some examples, the outside facing surfaces of the flanges are approximately coincident with the angled pilot holes (e.g., pilot hole 604), as the implant is advanced into the bone.

Figure 13:
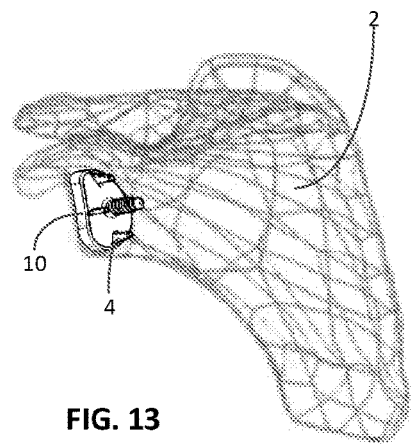

Implant 10 is then held in place as needed until it becomes fixed in place on the glenoid as shown in FIG. 13. Fixation occurs upon curing of the bone cement on post 34 and through the friction fit of each flange within cancellous bone 8. Over a longer duration of time, bone ingrowth between the inner sublayer of implant 10 and the bone provides additional fixation, as described in greater detail below.

Turning to the position of implant 10 relative to the glenoid vault when fixed to the glenoid vault, a close up view of the implant in its final secure position on glenoid 4 is shown in FIG. 14. Tapered surfaces of each flange are nearly tangent to the contour of cortical bone wall 7 of vault 6, while not breaching the cortical bone. In this manner, the flanges are positioned as close as possible to the outer perimeter of the vault without contacting or damaging the cortical bone. In some examples, outside surface 42A of flange 40A is from about 0.5 mm to about 1.5 mm from an inside surface of cortical bone wall 7. In some examples, outside surface 42A is from about 0.8 mm to about 1.0 mm from inside surface of cortical bone wall 7. In still further examples, outside surface 42A is approximately 0.9 mm from the inside surface of cortical bone wall 7.

Continuing to refer to the implant in the fixed position on the glenoid vault, dimensions P1 and P2 denote distances from a base of outside surface 42A of flange 40A to an outer perimeter of the external wall of the glenoid vault and an outer perimeter of the implant, respectively. P1 may be from about 2 mm to about 10 mm. In some examples, P1 may be from about 4 mm to about 8 mm. P2 may be from 0 mm to about 8 mm. When P2 is 0 mm, the base of the outside surface of the flange may be flush with the outer perimeter of the implant. In some examples, P1 equals P2. It should be appreciated that these ranges of dimensions may apply to each flange of the implant. Exact dimensions, such as P1 and P2, for a particular flange on an implant may be established as a function of the geometry of the bone receiving the implant.

As noted elsewhere in the disclosure, the peripheral positioning of the flanges on the implant provides for greater load sharing/distribution than other implants with more centrally positioned flanges. Further, the large surface area of metal layer 30 provides an improved connection between the polymer layer and the metal layer than with other hybrid designs having metal layers with smaller surface areas.

During regular use of the implant following completion of the surgery, i.e., following implant fixation into the joint, the glenoid undergoes regular, repeated loading, and micromotion occurs between the inner sublayer of metal layer 30 and the bone. This micromotion promotes bone ingrowth into the inner sublayer. A similar process of bone ingrowth occurs between a porous outer region of the flanges and the bone. In this manner, the fixation of the implant to the bone strengthens over time, improving the longevity of the implant. In contrast, a bond for implants secured to bone via cement tends to break down over time. Thus, in addition to improved load sharing across the implant structure, the implants of the present disclosure have greater longevity relative to other glenoid implants, hybrid or otherwise, that rely on cement for fixation.

In some variations of the method, advancing the glenoid implant into the bone involves directing each of the plurality of flanges closer to a tangent position relative to the inner cortical bone surface of the glenoid vault. In some variations, drilling the second pilot hole involves aligning a drill so that the trajectory of the drill for the second pilot hole is offset from an inner cortical bone surface of a cortical bone defining a glenoid vault at least to a depth of 10 mm below a surface of the glenoid bone.

It should be appreciated that implants 310, 410 of the present disclosure may be fixed to a glenoid in the same manner as described for implant 10.

In another embodiment, a method of fixing an implant to a glenoid is performed with an implant having flanges 140 with tapers on opposing sides. This method is performed largely in the same manner as the method of fixing implant 10, though each pair of pilot holes for each flange may be tapered in opposite directions to complement the flange shape.

In yet another embodiment, the method of fixing an implant to a glenoid is performed with implant 210 shown in FIGS. 6-8. Unless otherwise noted, the method steps are the same as those described for implant 10. Due to the geometry of flanges 240A-D, each flange has a blade-like sharp tip. In this manner, preparation of the glenoid surface for receipt of the implant only involves drilling of a single central pilot hole for receipt of central post 234. Then, implant 210 is advanced onto the glenoid (not shown). Following contact with the bone, each flange advances into the cancellous bone as the sharp tip of each flange creates a pathway. Alternatively, pre-drilling (for pilot holes) or broaching may be optionally performed prior to advancing the flanges into the bone.

Another aspect of the present disclosure relates to a kit including one or more items. In one embodiment, a kit includes a single polymer component and a single metal component of an implant. In one embodiment, a kit includes one or more polymer components or one or more metal components. In yet another embodiment, a kit includes any number of polymer and metal components. In any one of the above embodiments, bone cement may be included with the kit. In any one of the above embodiments, surgical accessories and instruments used for placement and securement of the implant may be included with the kit.

It is contemplated that the elements of a given kit may be sorted into any subgroups desired, where each subgroup may be packaged separately. Of course, each item of a kit may also be individually packaged. For example, a polymer component and a metal component may be packaged separately. Through packaging each item in the kit separately or in different combinations, sterility of each item within the kit in the preparation for surgery is promoted. In some examples, the kits contemplated herein may be accompanied by an instruction manual on how to perform one or more of the methods of using the contents of the kit.

In yet another aspect, it should be noted that any of the devices and methods disclosed herein may be used in conjunction with robotic technology. For example, any of the implants described herein can be used with robotic surgical systems to perform an implantation procedure. The implants can be manipulated with a robotic system or a robotic arm to rotate, position, and secure the implant during a procedure. Further, any or all of the steps described in the methods for performing an implantation procedure of the present disclosure may be performed using a robotic system.

Although the invention herein has been described with reference to particular embodiments, it is to be understood that these embodiments are merely illustrative of the principles and applications of the present disclosure. It is therefore to be understood that numerous modifications may be made to the illustrative embodiments and that other arrange-

The invention claimed is:

1. A glenoid implant for use in a glenoid of a shoulder joint comprising:
   a body with a bearing surface and a bone-contacting surface opposite the bearing surface, the body extending from a superior end to an inferior end; and
   a plurality of flanges including a first flange, a second flange, a third flange and a fourth flange, each flange of the plurality of flanges extending from the bone-contacting surface of the body,
   the first flange extending from the bone-contacting surface of the body to a first free end, the first flange including a first inside facing surface that faces a center of the body and a first outside facing surface that faces an outer perimeter of the body, the first outside facing surface being opposite the first inside facing surface, each of the first inside and outside facing surfaces extending from the bone-contacting surface to the first free end,
      wherein the first outside facing surface at the bone-contacting surface of the body is 8 mm or less from the outer perimeter of the body,
      wherein the first outside facing surface is tapered from the bone-contacting surface toward the first free end,
      wherein the first inside facing surface is non-parallel to the first outside facing surface,
      wherein the first flange has a first oblong perimeter adjacent to the bone-contacting surface, a first linear axis being aligned with a long dimension of the first oblong perimeter, and
   the second flange extending from the bone-contacting surface of the body to a second free end, the second flange including a second inside facing surface that faces the center of the body and a second outside facing surface that faces the outer perimeter of the body, the second outside facing surface being opposite the second inside facing surface,
      wherein the second flange has a second oblong perimeter adjacent to the bone-contacting surface, a second linear axis being aligned with a long dimension of the second oblong perimeter, and
   wherein the first linear axis is transverse to the second linear axis,
   wherein the plurality of flanges are symmetrical about a central plane passing through a thickness direction of the body and a superior-inferior central axis of the body, the superior-inferior central axis passing through the superior end and the inferior end,
   wherein the first flange of the plurality of flanges is positioned at the superior end of the bone-contacting surface of the body and the third flange of the plurality of flanges is positioned at the inferior end of the bone-contacting surface of the body; and
   wherein respective free ends of the first, second, third, and fourth flanges each lie on a first plane, the first plane being perpendicular to a length dimension of the first flange between the bone-contacting surface and the first free end.

2. The glenoid implant of claim 1, wherein the second flange and the fourth flange extend from a periphery of the bone-contacting surface of the body.

3. The glenoid implant of claim 1, wherein the first outside facing surface of the first flange at the bone-contacting surface of the body is between 2 mm and 6 mm from the outer perimeter of the body.

4. The glenoid implant of claim 1, wherein the first outside facing surface of the first flange is planar from the bone-contacting surface to the first free end.

5. The glenoid implant of claim 1, wherein the first outside facing surface of the first flange is arcuate from the bone-contacting surface to the first free end.

6. The glenoid implant of claim 1, wherein the first flange has a thickness measured from the first inside facing surface to the first outside facing surface, the thickness being within a range of 3 mm to 5 mm at the bone-contacting surface of the body and within a range of 2 mm to 4 mm at the first free end of the first flange.

7. The glenoid implant of claim 6, wherein the first inside facing surface and the first outside facing surface of the first flange are connected by side surfaces, and a distance between the side surfaces is within a range of 2 mm to 4 mm.

8. The glenoid implant of claim 1, wherein the length dimension of the first flange is within a range from 4 mm to 10 mm.

9. A glenoid implant for use in a shoulder joint comprising:
   an outer layer with a first material property, the outer layer being configured to articulate with a first native or prosthetic bone of the shoulder joint;
   an inner layer fixed to the outer layer, the inner layer adapted for engagement with a bearing surface of a second native or prosthetic bone of the shoulder joint, the inner layer having a second material property different from the first material property;
   a plurality of flanges consisting of a first flange, a second flange, a third flange and a fourth flange, each flange of the plurality of flanges extending from an inner surface of the inner layer,
   the first flange having a first outside facing surface that faces an outer perimeter of the inner layer and a first inside facing surface that faces a center of the inner surface of the inner layer, the first outside facing surface and the first inside facing surface being separated by a first pair of side surfaces, wherein the first outside facing surface includes a flat planar portion that is coincident with a first plane, the first inside facing surface is coincident with a second plane, and one surface of the first pair of side surfaces includes a flat planar portion that is coincident with a third plane,
      wherein the first plane and the second plane are non-parallel, and
   the second flange having a second outside facing surface that faces the outer perimeter of the inner layer and a second inside facing surface that faces the center of the inner surface of the inner layer, the second outside facing surface and the second inside facing surface being separated by a second pair of side surfaces, wherein the second outside facing surface includes a flat planar portion that is coincident with a fourth plane and one surface of the second pair of side surfaces includes a flat planar portion that is coincident with a fifth plane,
   wherein the first plane is transverse to the fourth plane and the third plane is transverse to the fifth plane, and
   wherein the first flange is disposed on a superior-most end of the inner surface, the second flange is disposed on an anterior-most end of the inner surface, the third flange is disposed on an inferior-most end of the inner surface and the fourth flange is disposed on a posterior-most end of the inner surface, the flanges being spaced apart at peripheral locations on the inner layer to correspond to respective superior-most, anterior-most, inferior-most and posterior-most ends of the second native or prosthetic bone of the shoulder joint when the glenoid implant is disposed on the second native or prosthetic bone.

10. The glenoid implant of claim 9, wherein the inside facing surfaces of two of the first, second, third and fourth flanges are parallel to one another.

11. The glenoid implant of claim 10, wherein the outside facing surfaces of each of the first, second, third and fourth flanges are tapered toward respective free ends of the flanges relative to the inside facing surfaces of the flanges.

12. The glenoid implant of claim 9, wherein the first outside facing surface of the first flange at the inner surface of the inner layer is 6 mm or less from an outer edge of the outer layer.

13. The glenoid implant of claim 9, wherein the outer layer is a polymer and the inner layer is a metal.

14. The glenoid implant of claim 13, wherein the inner layer includes a central opening therethrough such that a central post of the outer layer passes through the central opening, the central post configured to be inserted into the second native or prosthetic bone of the shoulder joint.

15. The implant of claim 9, wherein the inside facing surfaces of the first flange and the second flange are perpendicular to one another.

16. An implant for use in a mammalian joint comprising:
an outer layer with a joint facing surface and a bone facing surface;
an inner layer with a joint facing surface and a bone facing surface, the joint facing surface of the inner layer fixed to the bone facing surface of the outer layer, the inner layer having a length extending from a superior end to an inferior end;
a plurality of flanges including a first flange, a second flange, a third flange and a fourth flange, each flange of the plurality of flanges extending from the bone facing surface of the inner layer;
the first flange comprising a length extending from a first base at the bone facing surface of the inner layer to a first free end,
wherein the first flange includes a first outside surface that faces an outer perimeter of the inner layer and a first inside surface opposite the first outside surface that faces a center of the bone facing surface of the inner layer, both the first outside surface and the first inside surface extending along the length of the first flange,
wherein the first outside surface of the first flange at the bone facing surface of the inner layer is 8 mm or less from an outer perimeter of the outer layer, and
wherein the first outside surface and the first inside surface of the first flange are asymmetric about a first central longitudinal axis of the first flange such that a distance between the first outside surface and the first inside surface is greater at the first base than at the first free end, a first linear axis passing through the first outside and inside surfaces at the first base, and
the second flange comprising a length extending from a second base at the bone facing surface of the inner layer to a second free end, wherein the second flange includes a second outside surface that faces the outer perimeter of the inner layer and a second inside surface opposite the second outside surface that faces the center of the bone facing surface of the inner layer, both the second outside surface and the second inside surface extending along the length of the second flange,
wherein the second outside surface and the second inside surface of the second flange are asymmetric about a second central longitudinal axis of the second flange such that a distance between the second outside surface and the second inside surface of the second flange is greater at the second base than at the second free end, a second linear axis passing through the second outside and inside surfaces at the second base,
wherein the first linear axis is transverse to the second linear axis,
wherein the plurality of flanges are symmetrical about a central plane passing through a thickness direction of the inner layer and a superior-inferior central axis of the inner layer, the superior-inferior central axis passing through the superior end and the inferior end,
wherein the first flange of the plurality of flanges is positioned at the superior end of the bone facing surface of the inner layer and the third flange of the plurality of flanges is positioned at the inferior end of the bone facing surface of the inner layer; and
wherein respective free ends of the first, second, third, and fourth flanges each lie on a first plane, the first plane being perpendicular to a direction of the length of the first flange.

17. The implant of claim 16, wherein the first flange has a decreasing sectional dimension from the bone facing surface of the inner layer to the first free end.

18. The implant of claim 16, wherein the first outside surface of the first flange at the bone facing surface of the inner layer is 2 mm to 6 mm from the outer perimeter of the outer layer.

19. The implant of claim 18, wherein the first outside surface of the first flange at the bone facing surface of the inner layer is a first distance from both the outer perimeter of the inner layer and the outer perimeter of the outer layer.

* * * * *